United States Patent [19]

Neuzil et al.

[11] Patent Number: 4,533,398
[45] Date of Patent: Aug. 6, 1985

[54] EXTRACTION OF SUCROSE

[75] Inventors: Richard W. Neuzil, Downers Grove; Richard L. Fergin, Mt. Prospect, both of Ill.

[73] Assignee: UOP Inc., Des Plaines, Ill.

[21] Appl. No.: 544,903

[22] Filed: Oct. 24, 1983

Related U.S. Application Data

[60] Division of Ser. No. 308,013, Oct. 2, 1981, Pat. No. 4,426,232, which is a continuation-in-part of Ser. No. 246,349, Mar. 23, 1981, abandoned.

[51] Int. Cl.³ ............................................. C13D 3/12
[52] U.S. Cl. ........................................ 127/55; 210/674
[58] Field of Search ................... 127/46.3, 55, 46.2, 127/46.1; 210/691, 674

[56] References Cited

U.S. PATENT DOCUMENTS

| | | | |
|---|---|---|---|
| 2,528,058 | 10/1950 | Jordan | 127/46.2 |
| 2,549,840 | 4/1951 | Montgomery et al. | 127/55 |
| 3,720,626 | 3/1973 | Benzaria et al. | 210/674 |
| 3,935,006 | 1/1976 | Fischer | 210/674 |
| 4,073,747 | 2/1978 | Popper et al. | 210/674 X |
| 4,157,267 | 6/1979 | Odawara et al. | 127/46.2 |
| 4,312,678 | 1/1982 | Landis | 127/46.3 |
| 4,333,770 | 6/1982 | Neuzil et al. | 127/46.3 |
| 4,353,992 | 10/1982 | Panneke et al. | 210/674 X |

Primary Examiner—Ivars Cintins
Attorney, Agent, or Firm—Thomas K. McBride; Louis A. Morris; William H. Page, II

[57] ABSTRACT

Sucrose which is found in molasses such as beet molasses or cane molasses may be selectively extracted therefrom by passing an aqueous solution of the molasses over a solid adsorbent such as activated carbon. The sucrose will be selectively adsorbed thereon and separated from the betaine and mineral salts, specifically potassium chloride, in the molasses. The sucrose is then removed from the adsorbent by treatment with a desorbent material comprising an alcohol. An essential step in the process is the flushing of the desorbent from the adsorbent with water prior to the subsequent contact of the adsorbent with the feed stream.

1 Claim, 3 Drawing Figures

EXTRACTION OF SUCROSE

CROSS REFERENCE TO RELATED APPLICATIONS

This application is a division of my prior copending application Ser. No. 308,013 filed Oct. 2, 1981, now U.S. Pat. No. 4,426,232, issued Jan. 17, 1984 which is a continuation-in-part of my prior, copending application Ser. No. 246,349 filed Mar. 23, 1981, now abandoned. The above prior applications are incorporated herein by reference.

BACKGROUND OF THE INVENTION

1. Field of the Invention

The field of art to which this invention pertains is solid bed adsorptive separation. More specifically, the invention relates to a process for separating sucrose from an aqueous solution.

2. Prior Art

Sucrose, which is a common form of sugar, is widely used in the food industry. The usual source for this compound is found in the juice of sugar cane, sugar beets and other sucrosecontaining materials. After the readily recoverable sucrose has been extracted from these sources, the mother liquors which are generally termed "molasses" will still contain a relatively large amount of sucrose along with other sugars such as glucose, fructose, raffinose, etc. The latter compounds along with salts, amino acids, betaine, pyrollidone, carboxylic acid, etc. constitute crystallization inhibitors which make the recovery of the remaining sucrose difficult to accomplish and thus make the further recovery of the sucrose economically impractical. In addition, the impurities which are present impart a taste to the molasses which renders the same inedible for human consumption.

Sugar beet molasses may contain approximately 50% sucrose and, therefore, it is highly desirable to extract this sucrose from the aforesaid molasses. Inasmuch as hereinbefore set forth, the molasses is bitter to human taste, the residual molassses is used in animal feed or as a fertilizer, and therefore a relatively low sucrose content is an acceptable feature of the molasses. At the present time there are only a few methods for extracting the sucrose present in molasses from the compounds of the type hereinbefore set forth. One such process which is utilized is the Steffan's process in which the beet molasses is diluted to about 20% solids, refrigerated, and treated with a calcium compound such as calcium oxide. This results in the reaction of the sucrose present with a calcium oxide to form tricalcium sucrate which is an insoluble granular precipitate. This precipitate can then be removed from the diluted molasses solution by filtration followed by washing, to remove adhering impurities. The tricalcium sucrate is returned to the beet processing operation by adding to the incoming hot beet juice. Under such conditions the tricalcium sucrate decomposes, releasing the sucrose to solution so that the calcium oxide has acted as a purification agent. However, a disadvantage which is inherent in the process is that certain impurities are recycled, particularly raffinose, which is a trisaccharide material. With the continual recycling of the tricalcium sucrate the amount of raffinose present begins to accumulate and, as hereinbefore discussed, will retard the desired crystallization of the sucrose, thus making it necessary to discard a certain amount of circulating molasses from time to time.

In addition to the Steffan process it is also possible to separate sucrose by utilizing non-continuous chromatographic procedures which employ ion exchange resins to isolate sucrose from the molasses. However, neither of the procedures results in a complete separation of the sucrose even though high purity can be obtained. The processes which effect this separation employ a strong acid, polystyrene ion exchange resin in the alkaline or alkaline earth form and typically are as described by H. J. HONGISTO (Technical Department, Finnish Sugar Company Ltd., Kantvik, Finland), "Chromatographic Separation of Sugar Solutions; The Finsugar Molasses Desugarization Process"; paper presented to the 23rd Tech. Conf., British Sugar Comp. Ltd., 1976; and by Dr. MOHAMMAD MUNIR (Central Laboratory, Suddeutsche Zucker AG., 6719 Obrigheim 5, Wormser Str. 1, Germany), "Molasses Sugar Recovery by Liquid Distribution Chromatography"; the *International Sugar Journal*, 1976, 78, 100–106. A disadvantage which is present in the prior art processes lies in the fact that they require periodic back-flushing and regeneration of the ion exchange resin.

It is also known that certain other solid adsorbents selectively adsorb sucrose from an aqueous solution. The sucrose may then be desorbed with alcohol or an alcohol solution. These adsorbents, however, also exhibit a strong affinity for the alcohol and the sucrose is unable to effectively displace the alcohol from the adsorbent in a subsequent adsorption step.

A process has now been discovered by which sucrose may be separated and recovered from an aqueous solution, particularly molasses, by an adsorption-desorption technique utilizing a solid adsorbent selective for sucrose and an alcohol desorbent, notwithstanding the fact that the adsorbent may also have a high affinity for the alcohol.

SUMMARY OF THE INVENTION

In brief summary, the invention is, in one embodiment, a cyclical process for separating sucrose from an aqueous solution of sucrose and at least one of the compounds comprising betaine and a mineral salt each cycle of which comprises: (a) contacting the mixture at adsorption conditions with a solid adsorbent exhibiting selectivity for the sucrose thereby selectively adsorbing the sucrose on the adsorbent; (b) recovering the sucrose from the adsorbent by desorption comprising alcohol; and (c) flushing the alcohol from the adsorbent with water.

A process for separating sucrose from an aqueous solution of sucrose and at least one of the compounds comprising betaine and a mineral salt which process comprises contacting at adsorption conditions the mixture with a solid adsorbent exhibiting selectivity for the sucrose, which process comprises the steps of: (a) maintaining net fluid flow through a column of the adsorbent in a single direction, which column contains at least three zones having separate operational functions occurring therein and being serially interconnected with the terminal zones of the column connected to provide a continuous connection of the zones; (b) maintaining an adsorption zone in the column, the zone defined by the adsorbent located between a feed inlet stream at an upstream boundary of the zone and a raffinate outlet stream at a downstream boundary of the zone; (c) maintaining a purification zone immediately upstream from the adsorption zone, the purification zone defined by the adsorbent located between an extract outlet stream at an upstream boundary of the purification zone and the feed inlet stream at a downstream boundary of the purification zone; (d) maintaining a desorption zone immediately upstream from the purification zone, the desorption zone defined by the adsorbent located between a desorbent inlet stream at an upstream boundary of the zone and the extract outlet stream at a downstream boundary of the zone; (e) passing the feed stream into the adsorption zone at adsorption conditions to effect the selective adsorption of sucrose by the adsorbent in the adsorption zone and withdrawing a raffinate outlet stream from the adsorption zone; (f) passing a desorbent comprising alcohol into the desorption zone at desorption conditions to effect the displacement of the sucrose from the adsorbent in the desorption zone; (g) withdrawing an extract stream comprising the sucrose and desorbent material from the desorption zone; (h) passing a water inlet stream into the adsorption zone downstream of the feed inlet stream to effect the flushing of the alcohol from the adsorbent in the adsorption zone; and (i) periodically advancing through the column of adsorbent in a downstream direction with respect to fluid flow in the adsorption zone the feed inlet stream, raffinate outlet stream, desorbent inlet stream, extract outlet stream and water inlet stream to effect the shifting of zones through the adsorbent and the production of extract outlet and raffinate outlet streams.

In still another embodiment, the invention is a process for separating sucrose from an aqueous solution of sucrose and at least one of the compounds comprising betaine and a mineral salt which process comprises contacting at adsorption conditions the mixture with a solid adsorbent exhibiting selectivity for the sucrose, which process comprises the steps of: (a) maintaining net fluid flow through a column of the adsorbent in a single direction, which column contains at least three zones having separate operational functions occurring therein and being serially interconnected with the terminal zones of the column connected to provide a continuous connection of the zones; (b) maintaining an adsorption zone in the column, the zone defined by the adsorbent located between a feed inlet stream at an upstream boundary of the zone and a raffinate outlet stream at a downstream boundary of the zone; (c) maintaining a purification zone immediately upstream from the adsorption zone, the purification zone defined by the adsorbent located between an extract outlet stream at an upstream boundary of the purification zone and the feed inlet stream at a downstream boundary of the purification zone; (d) maintaining a desorption zone immediately upstream from the purification zone, the desorption zone defined by the adsorbent located between a desorbent inlet stream at an upstream boundary of the zone and the extract outlet stream at a downstream boundary of the zone; (e) maintaining a buffer zone immediately upstream from the desorption zone, the buffer zone defined as the adsorbent located between the desorbent input stream at a downstream boundary of the buffer zone and a raffinate output stream at an upstream boundary of the zone; (f) passing the feed stream into the adsorption zone at adsorption conditions to effect the selective adsorption of sucrose by the adsorbent in the adsorption zone and withdrawing a raffinate outlet stream from the adsorption zone; (g) passing a desorbent comprising alcohol into the desorption zone at desorption conditions to effect the displacerent of the sucrose from the adsorbent in the desorption zone; (h) withdrawing an extract stream comprising the sucrose and desorbent material from the desorption zone; (i) passing a water inlet stream into the buffer zone at the upstream boundary of the zone to effect the flushing of the alcohol from the adsorbent in the buffer zone; and (j) periodically advancing through the column of adsorbent in a downstream direction with respect to fluid flow in the adsorption zone, the feed inlet stream, raffinate outlet stream, desorbent inlet stream, extract outlet stream and water inlet stream to effect the shifting of zones through the adsorbent and the production of extract outlet and raffinate outlet streams.

Other objects and embodiments of the invention encompass details about feed mixtures, adsorbents, process schemes, desorbent materials and operating conditions, all of which are hereinafter disclosed in the following discussions of each of the facets of the present invention.

DETAILED DESCRIPTION OF THE INVENTION

Figure 1:
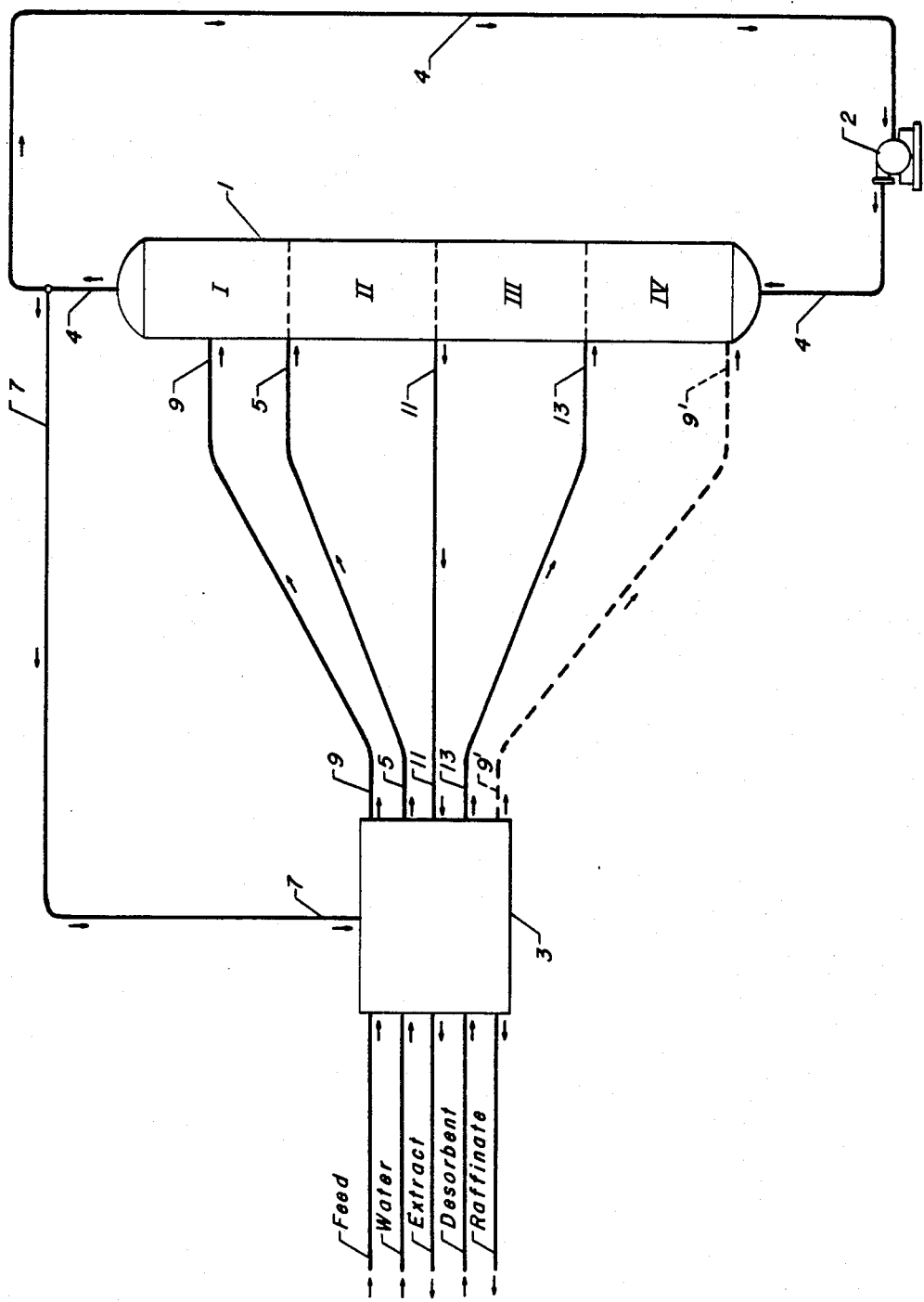
FIG. 1 represents, in schematic form, the embodiment of the present invention incorporating a simulated moving bed, hereinafter described, including adsorption column 1, manifold system 3 and various interconnecting lines.

This invention relates to a process for separating sucrose from an aqueous solution of sucrose and at least one of the compounds comprising betaine and a mineral salt. More specifically, the invention is concerned with a process for separating and recovering sucrose from a sugar source and still permitting the source such as molasses to be utilized in other fields such as for fertilizers or animal feed. However, the presence of other components which act as crystallization inhibitors make the recovery of sucrose relatively difficult to accomplish in a process based on crystallization.

In this process the presence of another sugar, such as raffinose (comprising about 1 wt. % of a molasses having a sucrose content of 51 wt. %), presents no problem since the other sugar will be separated with the sucrose and the product stream will comprise the sugar mixture. Other components of molasses, such as the color imparting bodies will also be separated with the sucrose. If desired, the raffinose may be removed from the feed or product streams by methods known to the art, such as enziomatic conversion which cleaves the tri-saccharide raffinose structure to the more desirable mono- and di-saccharides. The color bodies may be removed by high capacity activated carbon filters. The process of the present invention is effected by passing the feed mixture over an adsorbent of the type hereinafter set forth in greater detail. The passage of the feed stream over the adsorbent will result in the adsorption of sucrose while permitting the other components of the feed stream to pass through the treatment zone in an unchanged condition. Thereafter the sucrose will be desorbed from the adsorbent by treating the adsorbent with a desorbent material. Preferred adsorption and desorption conditions include a temperature in the range of from about 20° C. to about 200° C. and a pressure in the range of from about atmospheric to about 500 psig to ensure a liquid phase.

For purposes of this invention the various terms which are hereinafter used may be defined in the following manner.

A feed mixture is a mixture containing one or more extract components and one or more raffinate components to be separated by our process. The term "feed stream" indicates a stream of a feed mixture which passes to the adsorbent used in the process.

An "extract component" is a compound or type of compound that is more selectively adsorbed by the adsorbent while a "raffinate component" is a compound or type of compound that is less selectively adsorbed. The term "desorbent material" shall mean generally a material capable of desorbing an extract component. The term "desorbent stream" or "desorbent input stream" indicates the stream through which desorbent material passes to the adsorbent. The term "raffinate stream" or "raffinate output stream" means a stream through which a raffinate component is removed from the adsorbent. The composition of the raffinate stream can vary from essentially 100% desorbent material to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. At least a portion of the extract stream and preferably at least a portion of the raffinate stream from the separation process are passed to separation means, typically fractionators, where at least a portion of desorbent material is separated to produce an extract product and a raffinate product. The terms "extract product" and "raffinate product" mean products produced by the process containing, respectively, an extract component and a raffinate component in higher concentrations than those found in the extract stream and the raffinate stream.

One adsorbent which may be employed to selectively adsorb sucrose from an aqueous solution containing betaine and mineral salts comprises activated carbon. An activated carbon found to be effective as an adsorbent in the present invention was acquired from Pittsburgh Activated Carbon, a division of Calgon Corporation, a subsidiary of Merck & Co., Inc., and is known as "Calgon Activated Carbon". This activated carbon comprises high temperature steam activated coal. It is in a granular form of from 20 to 40 mesh size and has an ash content of 8 wt. %.

The carbonaceous material contemplated for use as an adsorbent in the present invention is manufactured by the Rohm and Haas Company and is sold under the trade name "Ambersorb". Examples of Ambersorb carbonaceous adsorbents are referred to in Rohm and Haas Company literature as Ambersorb XE-340, XE-347 and XE-348, and described in the literature as "hard, non-dusting, black spheres whose chemical composition is intermediate between that of activated carbon and polymeric adsorbents". The types differ in physical properties such as surface area, bulk density, particle size, pore volume and pore size distribution.

The porous polymeric material which may be used in the process of this invention as an adsorbent will comprise hydrophobic insoluble crosslinked polystyrene polymers, preferably those manufactured by the Rohm and Haas Company and sold under the trade name "Amberlite". Examples of Amberlite polymers are referred to in Rohm and Haas Company literature as Amberlite XAD-2 and Amberlite XAD-4, and described in the literature as "hard, insoluble spheres of high surface area, porous polymer". The various types of Amberlite polymeric adsorbents differ in physical properties such as porosity volume, surface area, average pore diameter, skeletal density and nominal mesh sizes.

Carbonaceous pyropolymers, useful as adsorbents in this invention, comprise shaped replications of particle aggregates containing recurring units of at least carbon and hydrogen atoms. The shaped replications are prepared by treating an inorganic support of the desired shape such as spheres, plates, pellets, rods, fibers, monoliths, etc., with a pyropolymer precursor and thereafter pyropolymerizing said precursor by treatment at an elevated temperature which may range from about 400° C. to about 1200° C. to form at least a monolayer of a carbonaceous pyropolymer possessing recurring units containing at least carbon and hydrogen atoms on the surface of said inorganic support. The carbonaceous pyropolymer will adopt the shape of the inorganic support and thus be a replication of the starting inorganic support material. It is preferred that the inorganic support material be characterized as having a surface area of from 1 to about 500 $m^2/g$. Illustrative examples of refractory oxides which may be employed include alumina in various forms such as gamma-alumina, eta-alumina, theta-alumina, or mixtures of inorganic refractory oxides such as zeolites, silica-alumina, silica-zirconia, zirconia-titania, zirconia-alumina, etc.

The feed mixtures which are charged to the process of the present invention will comprise sugar sources, a specific source which is utilized in the present invention comprising molasses. Molasses is the mother liquor remaining from the juice of sugar cane or beet, i.e. "thick juice", after removal by crystallization of most of the sucrose therefrom. As hereinbefore discussed, molasses such as cane molasses or sugar beet molasses will contain about 50% sucrose as well as other sugars such as glucose, fructose, raffinose as well as mineral salts and alkaloids, betaine, said other sugars and compounds being present in varying amounts in the sugar source. The most prevalent mineral salt in molasses is potassium chloride. The adsorbent of the present invention is chosen to selectively adsorb sucrose while allowing the betaine and the mineral salts, in the sugar source to pass through the system unchanged, i.e. the adsorbent of this invention possesses the necessary adsorbent character in the ability of the adsorbent to separate components of the feed, that is that the adsorbent possesses adsorptive selectivity for one component as compared to other components. Relative selectivity can be expressed not only for one feed compound as compared to another but can also be expressed between any feed mixture component and the desorbent material. The selectivity, (B), as used throughout this specification is defined as the ratio of the two components of the adsorbed phase over the ratio of the same two components in the unadsorbed phase at equilibrium conditions. Relative selectivity is shown as Equation 1, below.

$$\text{Selectivity} = (B) = \frac{[\text{wt. percent } C/\text{wt. percent } D]_A}{[\text{wt. percent } C/\text{wt. percent } D]_U} \quad \text{Equation 1}$$

where C and D are two components of the feed represented in weight percent and the subscripts A and U represent the adsorbed and unadsorbed phases respectively. The equilibrium conditions are determined when the feed passing over a bed of adsorbent does not change composition after contacting the bed of adsorbent. In other words, there is no net transfer of material occurring between the unadsorbed and adsorbed phases. Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally desorbent materials should have a selectivity equal to about 1 or slightly less than 1 with respect to all extract components so that all of the extract components can be desorbed as a class with reasonable flow rates of desorbent material, and so that extract components can displace desorbent material in a subsequent adsorption step. While separation of an extract component from a raffinate component is theoretically possible when the selectivity of the adsorbent for the extract component with respect to the raffinate component is greater than 1, it is preferred that such selectivity approach a value of 2. Like relative volatility, the higher the selectivity the easier the separation is to perform. Higher selectivities permit a smaller amount of adsorbent to be used. The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

Desorbent materials used in various prior art adsorptive separation processes vary depending upon such factors as the type of operation employed. In the swing-bed system, in which the selectively adsorbed feed component is removed from the adsorbent by a purge stream, desorbent selection is not as critical and desorbent material comprising gaseous hydrocarbons such as methane, ethane, etc., or other types of gases such as nitrogen or hydrogen, may be used at elevated temperatures or reduced pressures or both to effectively purge the adsorbed feed component from the adsorbent. However, in adsorptive separation processes which are generally operated continuously at substantially constant pressures and temperatures to insure liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity (hereinafter discussed in more detail), it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent in admixture with desorbent material and any chemical reaction involving a desorbent material and an extract component or a raffinate product or both. Since both the raffinate stream and the extract stream typically contain desorbent materials, desorbent materials should additionally be substances which are easily separable from the feed mixture that is passed into the process. Without a method of separating at least a portion of the desorbent material present in the extract stream and the raffinate stream, the concentration of an extract component in the extract product and the concentration of a raffinate component in the raffinate product would not be very high, nor would the desorbent material be available for reuse in the process. It is contemplated that at least a portion of the desorbent material will be separated from the extract and the raffinate streams by distillation or evaporation, but other separation methods such as reverse osmosis may also be employed alone or in combination with distillation or evaporation. Since the raffinate and extract products are foodstuffs intended for human consumption, desorbent materials should also be non-toxic. Finally, desorbent materials should also be materials which are readily available and therefore reasonable in cost.

The desorbent material found to be most effective in desorbing the sucrose comprises alcohol, particularly alcohol in aqueous solution in which the alcohol comprises from about 10 vol. % to about 70 vol. % of the solution. The most preferred alcohols are methanol and ethanol, but ethanol is particularly preferred because it is safe to use with food products, i.e. the products obtained from the process of the present invention are likely to be used for human or animal consumption. The problem when alcohol is so used is that the adsorbent has a high affinity for alcohol and as a result the sucrose is unable to effectively displace the alcohol, particularly ethanol, from the adsorbent when the adsorbent is re-used in the adsorption step. This inability results in a substantial loss of sucrose into the raffinate. In spite of this high affinity of the adsorbent for the alcohol, the surprising observation has been made that water is very effective in displacing the alcohol from the adsorbent and if a water flush step is included between the desorption and adsorption steps, adsorption of the sucrose will efficiently occur in an alcohol-free environment. We thus have the presently inexplicable phenomena that although water will not efficiently displace sucrose from the adsorbent, alcohol will, but, on the other hand, water accomplishes what sucrose cannot, i.e. displace alcohol, at least to the extent and in a manner that leaves the adsorbent in a form receptive to sucrose.

A dynamic testing apparatus is employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of sucrose and of a particular crystallization inhibitor(s) all diluted in desorbent is injected for a duration of several minutes. Desorbent flow is resumed, and the sucrose and the crystallization inhibitors are eluted as in a liquid-solid chromatographic operation. The effluent can be analyzed on-stream or alternatively effluent samples can be collected periodically and later analyzed separately by analytical equipment and traces of the envelopes of corresponding component peaks developed.

From information derived from the test adsorbent performance can be rated in terms of void volume, retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance between the peak envelopes. Selectivity, (B), for an extract component with respect to a raffinate component may be characterized by the ratio of the distance between the center of the extract component peak envelope and the tracer peak envelope (or other reference point) to the corresponding distance between the center of the raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

The adsorbent may be employed in the form of a dense compact fixed bed which is alternatively contacted with the feed mixture, desorbent materials and water flush. In the simplest embodiment of the invention the adsorbent is employed in the form of a single static bed in which case the process is only semi-continuous. In another embodiment a set of two or more static beds may be employed in fixed-bed contacting with appropriate valving so that the feed mixture is passed through one or more adsorbent beds while the desorbent materials and water flush can be passed through one or more of the other beds in the set. The flow of feed mixture, desorbent materials and water flush may be either up or down through the desorbent. Any of the conventional apparatus employed in static bed fluid-solid contacting may be used.

Countercurrent moving bed or simulated moving bed countercurrent flow systems, however, have a much greater separation efficiency than fixed adsorbent bed systems and are therefore preferred. In the moving bed or simulated moving bed processes the adsorption, desorption and flushing operations are continuously taking place which allows both continuous production of an extract and a raffinate stream and the continual use of feed, desorbent and flush streams. One preferred embodiment of this process utilizes what is known in the art as the simulated moving bed countercurrent flow system. The operating principles and sequence of such a flow system are described in U.S. Pat. No. 2,985,589, incorporated herein. In such a system it is the progressive movement of multiple liquid access points down an adsorbent chamber that simulates the upward movement of adsorbent contained in the chamber. Only five of the access lines are active at any one time; the feed input stream, desorbent inlet stream, water flush inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of the process it is generally necessary that three separate operational zones be present in order for the process to take place although in some instances an optional fourth zone may be used. There is a net positive fluid flow through all portions of the column in the same direction, although the composition and rate of the fluid will, or course, vary from point to point. With reference to FIG. 1, zones I, II, III and IV are shown as well as manifold system 3, pump 2, which maintains the net positive fluid flow, and line 4 associated with pump 2. Also shown and identified are the inlet and outlet lines to the process which enter or leave via manifold system 3.

The adsorption zone, zone I, is defined as the adsorbent located between the feed inlet stream 5 and the raffinate outlet stream 7. In this zone, the feedstock contacts the adsorbent, an extract component is adsorbed, and a raffinate stream is withdrawn. Since the general flow through zone I, in accordance with the direction of fluid flow throughout the column, is from the feed stream which passes into the zone to the raffinate stream which passes out of the zone, the flow in this zone is considered to be a downstream direction when proceeding from the feed inlet to the raffinate outlet streams. The water flush stream 9 may be introduced in zone I at a point slightly downstream of the feed inlet stream. The water will be added at a rate sufficient to displace the alcohol associated with the packed bed of adsorbent in simulated movement in zone I, thereby facilitating the adsorption of the sucrose.

Immediately upstream with respect to fluid flow in zone I is the purification zone, zone II. The purification zone is defined as the adsorbent between the extract outlet stream 11 and the feed inlet stream 5. The basic operations taking place in zone II are the displacement from the non-selective void volume of the adsorbent of any raffinate material carried into zone II by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone III into zone II at zone II's upstream boundary, the extract outlet stream, to effect the displacement of raffinate material. The flow of material in zone II is in a downstream direction from the extract outlet stream to the feed inlet stream.

Immediately upstream of zone II with respect to the fluid flowing in zone II is the desorption zone or zone III. The desorption zone is defined as the adsorbent between the desorbent inlet 13 and the extract outlet stream 11. The function of the desorption zone is to allow a desorbent material which passes into this zone to displace the extract component which was adsorbed upon the adsorbent during a previous contact with feed in zone I in a prior cycle of operation. The flow of fluid in zone III is essentially in the same direction as that of zones I and II.

In some instances an optional buffer zone, zone IV, may be utilized. This zone, defined as the adsorbent between the raffinate outlet stream 7 and the desorbent inlet stream 13, if used, is located immediately upstream with respect to the fluid flow to zone III. Zone IV would be utilized to conserve the amount of desorbent utilized in the desorption step since a portion of the raffinate stream which is removed from zone I can be passed into zone IV to displace desorbent material present in that zone out of that zone into the desorption zone. Zone IV will contain enough adsorbent so that raffinate material present in the raffinate stream passing out of zone I and into zone IV can be prevented from passing into zone III thereby contaminating extract stream removed from zone III. In the instances in which the fourth operational zone is not utilized the raffinate stream passed from zone I to zone IV must be carefully monitored in order that the flow directly from zone I to zone IV can be stopped when there is an appreciable quantity of raffinate material present in the raffinate stream passing from zone I into zone III so that the extract outlet stream is not contaminated.

In the most preferred embodiment of the present invention zone IV will be employed and the water flush stream 9 will be introduced not into zone I, but into zone IV at the upstream boundary of zone IV (shown as dotted line 9'). In this way the alcohol that would otherwise move into zone IV from zone III as part of the simulated moving adsorbent bed will be kept in zone III, assuming that the correct aaount of water flush is used. This will also reduce the alcohol-water desorbent requirements. Thus, when the adsorbent enters zone I, it will have the proper all water environment.

A cyclic advancement of the input and output streams through the fixed bed of adsorbent can be accomplished by utilizing a manifold system 3 in which the valves in the manifold are operated in a sequential manner to effect the shifting of the input and output streams thereby obtaining the effect of a flow of fluid with respect to a moving bed of solid adsorbent in a countercurrent manner although the bed itself is actually stationary. Another mode of operation which can effect the countercurrent flow of solid adsorbent with respect to fluid involves the use of a rotating disc valve in which the input and output streams are connected to the valve and the lines through which feed input, water flush input, extract output, desorbent input and raffinate output streams are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the adsorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the desorbent material can be separated to produce an extract product containing a reduced concentration of desorbent material. Preferably, but not necessary to the operation of the process, at least a portion of the raffinate output stream will also be passed to a separation means wherein at least a portion of the desorbent material can be separated to produce a desorbent stream which can be reused in the process and a raffinate product containing a reduced concentration of desorbent material. The separation means will typically be a fractionation column, the design and operation of which is well known to the separation art.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor-phase operation. Adsorption conditions will include a temperature range of from about 20° C. to about 200° C., with about 20° C. to about 100° C. being more preferred and a pressure range of from about atmospheric to about 500 psig with from about atmospheric to about 250 psig being more preferred to insure liquid phase. Desorption conditions will include the same range of temperatures and pressures as used for adsorption conditions.

The size of the units which can utilize the process of this invention can vary anywhere from those of pilot plant scale (see for example our assignee's U.S. Pat. No. 3,706,812) to those of commercial scale and can range in flow rates from as little as a few cc an hour up to many thousands of gallons per hour.

The following examples are given to illustrate the process of this invention, however, it is to be understood that these examples are given merely for purposes of illustration, and that the present invention is not necessarily limited thereto.

EXAMPLE I

The purpose of this example is to present the results of pulse tests obtained from the above described pulse test apparatus when using the aforementioned Calgon Activated Carbon. Feed pulses were 10 ml each and comprised 10 wt. % KCl, 10 wt. % betaine, 30 wt. % sucrose and 50 wt. % carrier material. The column was operated at 60° C.

Figure 2:
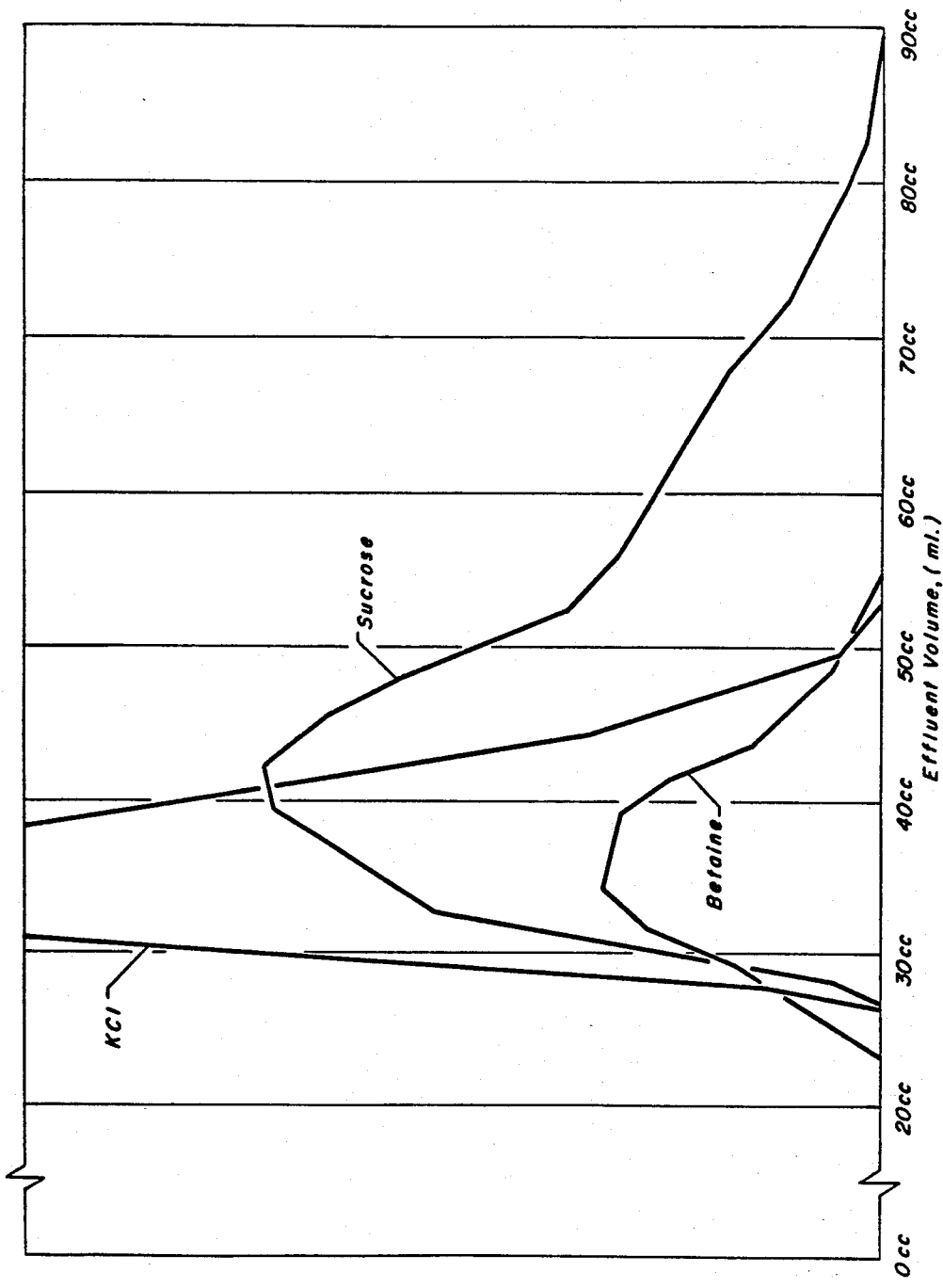
FIGS. 2 and 3 comprise graphical representations of data obtained for the following examples.

FIG. 2 shows the results of a first test where no water flush prepulse stream was used. The carrier material was 20 wt. % ethanol in water. As clearly shown in FIG. 2 a mediocre separation of sucrose from the other components was achieved. The sucrose was eluted last, which is indicative of it being the extract component, but only a small volume of the sucrose, free of contamination by the other components, was eluted.

Figure 3:
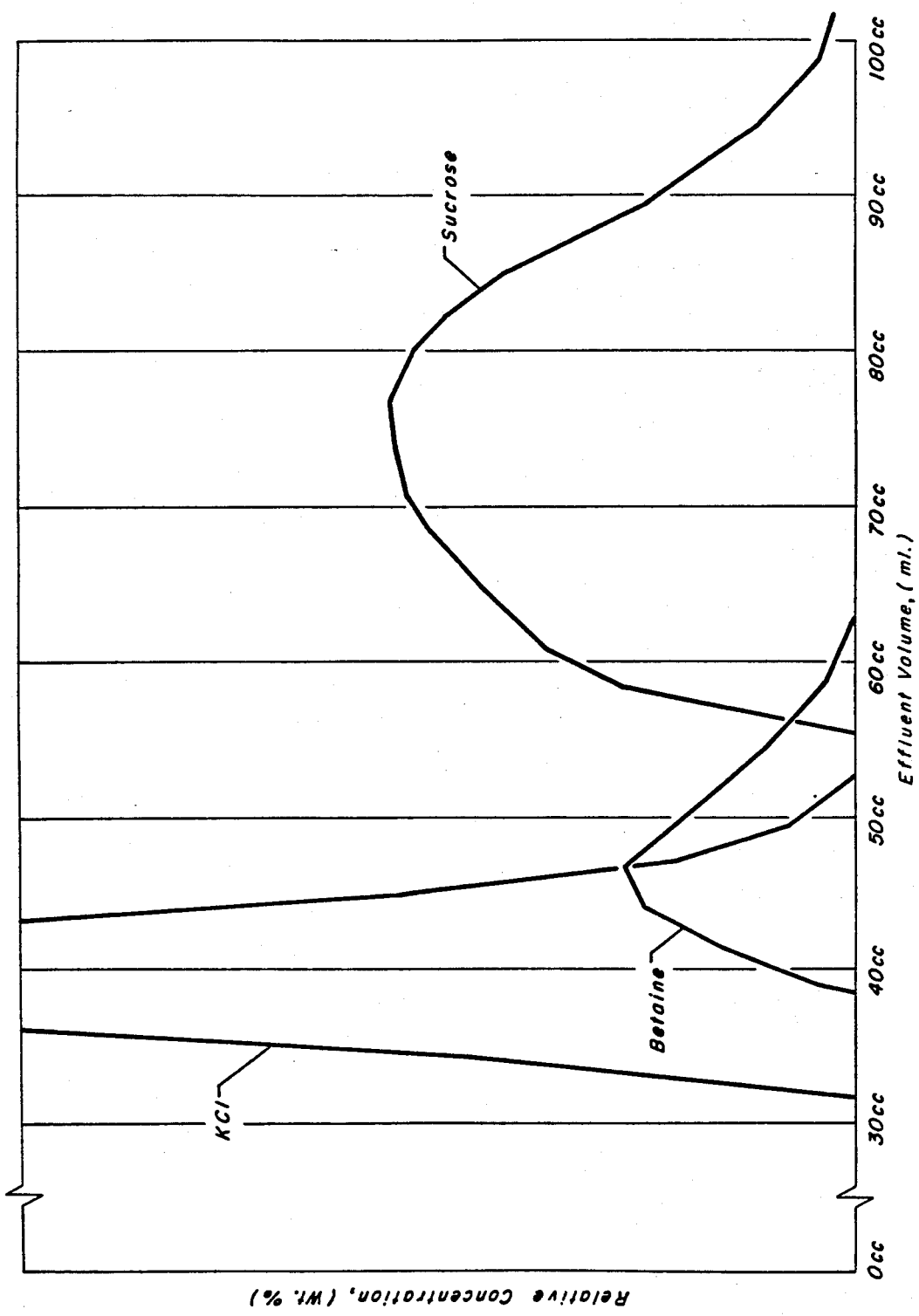

FIG. 3 shows the results of the second test which was in all respects conducted as the first test except that the carrier material was water and the column had previously undergone a desorption step with a 20 wt. % ethanol in water solution followed by a 40 cc water prepulse to simulate the process of the present invention. As clearly shown in FIG. 3, an excellent separation of sucrose from the other components may be achieved when alcohol has been flushed from the system. Almost the entire amount of sucrose in the feed pulse was retained by the adsorbent following elution of the other components.

In view of the foregoing tests it may be concluded that the adsorption of sucrose by the adsorbent is inhibited by the presence of ethanol, the preferred desorbent, but becomes almost ideal in an alcohol-free environment, i.e. an environment obtained by use of a water flush or prepulse step.

EXAMPLE II

This example presents the results of actual testing of the invention in a continuous countercurrent liquid-solid contacting device. The general operating principles of such a device have been previously described and are found in Broughton U.S. Pat. No. 2,985,589 and a specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed, desorbent and water flush are being introduced through three of the lines and raffinate and extract are withdrawn through two more. All remaining access lines are inactive and when the position of the distributing valve is advanced by one index, all active positions will be advanced by one bed. This simulates a condition in which the adsorbent physically roves in a direction countercurrent to the liquid flow. The equipment was set up to illustrate the preferred embodiment of the present invention in which a buffer zone, zone IV, is employed, with the water flush stream introduced at the upstream boundary of the buffer zone. Additional details on adsorbent testing and evaluation may be found in the paper "Separation of $C_8$ Aromatics by Adsorption" by A. J. de Rosset, R. W. Neuzil, A. J. Korous, and D. H. Rosback presented at the American Chemical Society, Los Angeles, Calif., Mar. 28 to Apr. 2, 1971. All of the above references are incorporated herein by reference.

In these tests the feedstock contained 30 wt. % sucrose, 10 wt. % KCl, 10 wt. % betaine and 50 wt. % water. The adsorbent used was the same as used in the tests of Example I. The water flush stream was introduced into zone IV at the rate of one void volume (of the adsorbent in zone IV) per cycle. The adsorbent used was 30 vol. % ethanol in water. Other details of the operation are as follows:

Volume of bed=460 ml
Valve Cycle Time=1 hr.
Process Temperature=65° C.
Feed Rate=72 cc/hr.=0.73 A/F (A=adsorbent selective pore volume, F=feed rate)

The results of the tests were a product (extract) purity of 99% sucrose was obtained at a yield of 90% and a purity of 95% sucrose was obtained at a yield of 99+%. The present invention was thus shown to be highly effective from the standpoints of both product purity and yield.

What is claimed is:

1. A cyclical process for separating sucrose from an aqueous solution of sucrose and at least one of the compounds comprising betaine and a mineral salt, each cycle of which process comprises:
   (a) contacting said mixture at adsorption conditions with a solid adsorbent exhibiting selectivity for said sucrose thereby selectively adsorbing said sucrose on said adsorbent;
   (b) recovering said sucrose from said adsorbent by desorption with a desorbent comprising alcohol; and thereafter
   (c) flushing said alcohol from said adsorbent with water.

* * * * *